United States Patent
Sakamoto et al.

(10) Patent No.: US 9,316,574 B2
(45) Date of Patent: *Apr. 19, 2016

(54) SENSOR CONTROLLER

(75) Inventors: Yuuki Sakamoto, Kariya (JP);
Mikiyasu Matsuoka, Kariya (JP);
Yuuzou Matsumoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 1050 days.

This patent is subject to a terminal disclaimer.

(21) Appl. No.: 13/183,585

(22) Filed: Jul. 15, 2011

(65) Prior Publication Data

US 2012/0034569 A1     Feb. 9, 2012

(30) Foreign Application Priority Data

Aug. 6, 2010 (JP) ................................ 2010-177511

(51) Int. Cl.
*F23N 5/00* (2006.01)
*G01N 15/06* (2006.01)

(52) U.S. Cl.
CPC ................................ *G01N 15/0656* (2013.01)

(58) Field of Classification Search
CPC .... G01N 15/0656; G01N 15/06; F01N 11/00; F01N 2550/12; F01N 2550/00; F02D 41/2474
USPC .......................................................... 431/76
See application file for complete search history.

(56) References Cited

U.S. PATENT DOCUMENTS

| | | | |
|---|---|---|---|
| 4,567,750 A * | 2/1986 | Artmann | G01N 27/16 340/627 |
| 4,656,832 A | 4/1987 | Yukihisa et al. | |
| 6,438,948 B2 * | 8/2002 | Ono | F02D 41/0055 60/278 |
| 6,634,210 B1 * | 10/2003 | Bosch | G01N 15/0656 204/426 |
| 6,735,941 B2 * | 5/2004 | Saito | F01N 3/023 60/291 |
| 6,907,873 B2 * | 6/2005 | Hamahata | F01N 9/002 123/676 |
| 7,051,519 B2 * | 5/2006 | Kuboshima | F01N 3/0231 60/286 |
| 7,147,688 B2 * | 12/2006 | Kondou | F01N 9/002 55/282.2 |
| 7,159,392 B2 * | 1/2007 | Kondoh | F01N 9/002 60/274 |
| 7,272,926 B2 * | 9/2007 | Kosaka | F01N 3/023 60/277 |
| 7,278,304 B2 * | 10/2007 | Zanini-Fisher | F01N 11/00 701/31.1 |

(Continued)

FOREIGN PATENT DOCUMENTS

| JP | 62-002146 | 1/1987 |
|---|---|---|
| JP | 2517537 | 4/1996 |

(Continued)

OTHER PUBLICATIONS

Office Action (2 pages) dated Jul. 23, 2013, issued in corresponding Japanese Application No. 2010-177511 and English translation (4 pages).

*Primary Examiner* — Shogo Sasaki
(74) *Attorney, Agent, or Firm* — Nixon & Vanderhye P.C.

(57) ABSTRACT

A sensor controller for a particulate matter detection sensor includes a heater configured to heat an attachment portion so as to burn and remove particulate matter attached to the attachment portion, a learning portion for obtaining a sensor detection value immediately after burning and removing the particulate matter due to heating of the heater. The leaning portion calculates a sensor standard value based on the obtained sensor detection value in a state where the particulate matter is removed, and stores the sensor standard value as a learning value. Furthermore, a correcting portion corrects the sensor detection value based on the sensor standard value stored by the learning portion.

12 Claims, 5 Drawing Sheets

(56) References Cited

U.S. PATENT DOCUMENTS

| | | | |
|---|---|---|---|
| 7,357,822 B2* | 4/2008 | Hamahata | F01N 13/009 55/282.2 |
| 7,458,206 B2* | 12/2008 | Yahata | F01N 9/002 60/274 |
| 7,574,895 B2* | 8/2009 | Schnell | G01N 15/0656 73/28.01 |
| 7,587,925 B2* | 9/2009 | Wirth | F01N 9/002 73/1.02 |
| 7,644,609 B2* | 1/2010 | Reutiman | G01N 15/0656 73/114.69 |
| 7,677,029 B2* | 3/2010 | Matsuno | F01N 3/0253 60/277 |
| 7,765,792 B2* | 8/2010 | Rhodes | F01N 3/027 60/276 |
| 2003/0230077 A1* | 12/2003 | Kuboshima | F01N 3/023 60/295 |
| 2007/0125075 A1* | 6/2007 | Zanini-Fisher | F01N 11/00 60/297 |
| 2007/0163233 A1* | 7/2007 | Cheng | F01N 3/021 60/277 |
| 2008/0264039 A1* | 10/2008 | Lattin | F01N 9/002 60/285 |
| 2012/0031078 A1 | 2/2012 | Sakamoto et al. | |

FOREIGN PATENT DOCUMENTS

| | | |
|---|---|---|
| JP | 2003-161440 | 6/2003 |
| JP | 2003-185614 | 7/2003 |
| JP | 2004-012352 | 1/2004 |
| JP | 2006-308440 | 11/2006 |
| JP | 2009-144577 | 7/2009 |

* cited by examiner

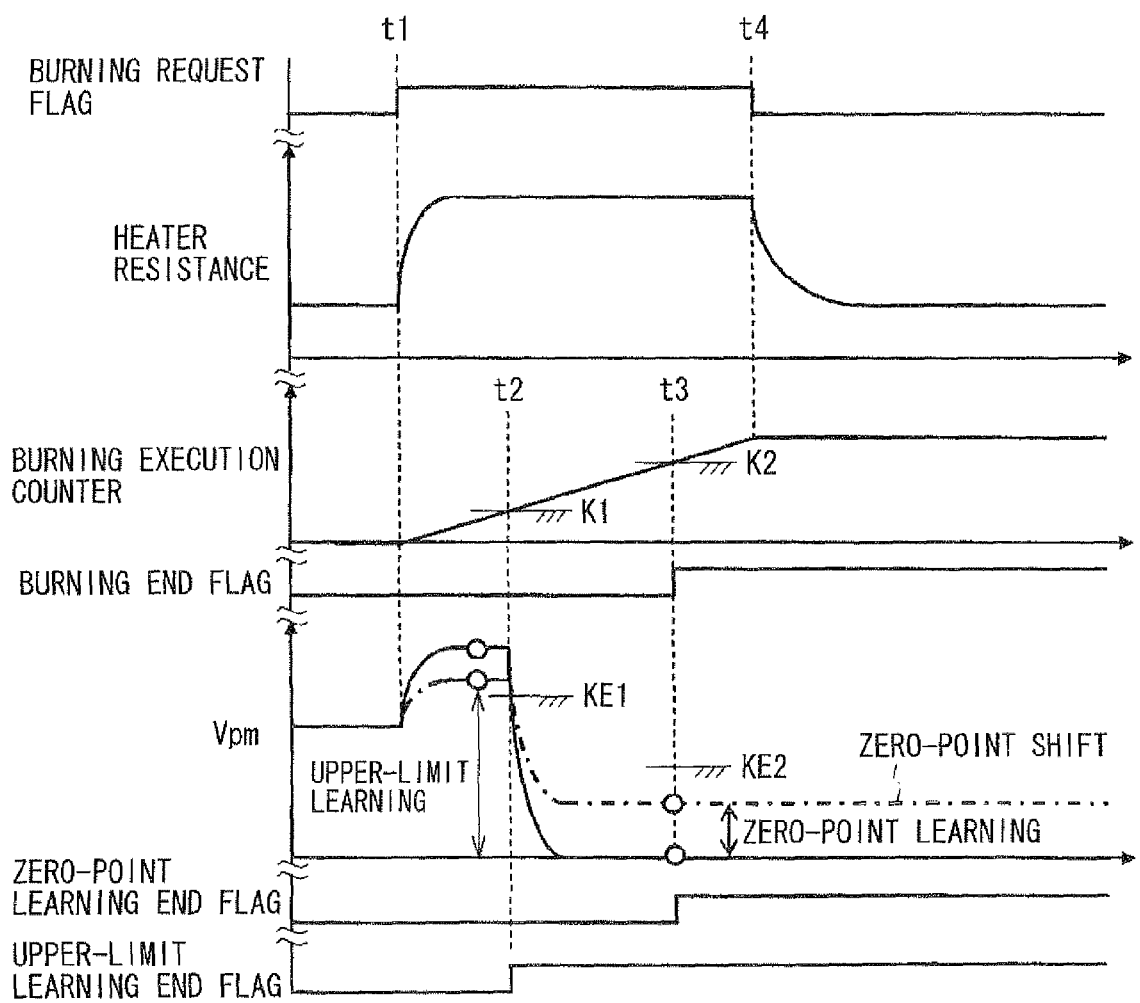

SENSOR CONTROLLER

CROSS REFERENCE TO RELATED APPLICATION

This application is based on Japanese Patent Application No. 2010-177511 filed on Aug. 6, 2010, the contents of which are incorporated herein by reference in its entirety.

TECHNICAL FIELD

The present invention relates to a sensor controller for calculating an amount of particulate matter (PM) based on a detection signal from a particulate matter detection sensor.

BACKGROUND

Various types of PM sensors (particulate matter detection sensors) for detecting the amount of PM exhausted from an engine or the like have been proposed. For example, a PM sensor disclosed in JP 59-196453A (corresponding to U.S. Pat. No. 4,656,832) includes a pair of opposed electrodes on an insulating substrate. The accumulation of PM changes a resistance between the pair of the electrodes. By using this property, the PM sensor is configured to detect the amount of PM by measuring the resistance between the electrodes. In this case, a detection circuit connected to a sensor element forms a voltage-dividing circuit configured by a resistance between the pair of opposed electrodes and a predetermined shunt resistance. The detection circuit is configured to output a voltage at an intermediate point of the voltage-dividing circuit as a sensor detected signal.

However, in the PM sensor and the detection circuit, a sensor difference, a variation in an elapsed time, a circuit error or the like may be caused, and thereby the PM amount may be incorrectly detected. For example, if a foreign matter such as a metal piece is attached to an insulating substrate of the PM sensor, or if a weak leakage current flows with the impurities in the insulating substrate, a sensor output which originally should not be produced may be caused, or the sensor output may become larger than a value originally assumed.

In view of the foregoing problems, it is an object of the present invention to provide a sensor controller which can effectively reduce a detection error of a particulate matter detection sensor (PM sensor) and can accurately detect the amount of particulate matter.

According to an aspect of the present invention, a sensor controller is adapted to a particulate matter detection sensor. The particulate matter detection sensor includes an attachment portion to which conductive particulate matter contained in gas is attached, and a pair of opposed electrodes spaced from each other at the attachment portion. Furthermore, the particulate matter detection sensor is adapted to output a detection signal corresponding to a resistance between the pair of opposed electrodes. The sensor controller is adapted to calculate an amount of attached particulate matter based on a sensor detection value from the particulate matter detection sensor. The sensor controller includes: a heater configured to heat the attachment portion so as to burn and remove the particulate matter attached to the attachment portion; learning means for obtaining the sensor detection value immediately after burning and removing the particulate matter due to heating of the heater, for calculating a first sensor standard value based on the obtained sensor detection value in a state where the particulate matter is removed from the attachment portion, and for storing the first sensor standard value as a first learning value; and correcting means for correcting the sensor detection value based on the first sensor standard value stored by the learning means. Here, the heater may include a heating unit for burning and removing the particulate matter by using the heat generated from the heater unit, and a heating means for heating the exhaust gas to a burning temperature of the particulate matter so as to burn the particulate matter, and the like.

Thus, even in a case where the first sensor standard value does not become a predetermined value that is set when the amount of attached particulate matter is zero, an error of the particulate matter detection sensor can be determined, and the sensor detection value can be accurately corrected. As a result, a detection error of a particulate matter detection sensor (PM sensor) can be effectively reduced, and thereby the amount of particulate matter can be accurately detected.

BRIEF DESCRIPTION OF THE DRAWINGS

Other objects, features and advantages of the present invention will become more apparent from the following description made with reference to the accompanying drawings, in which like parts are designated by like reference numbers and in which:

FIG. 5 is a timechart for explaining the output error learning process;

DETAILED DESCRIPTION OF THE PREFERRED EMBODIMENTS

Figure 1:
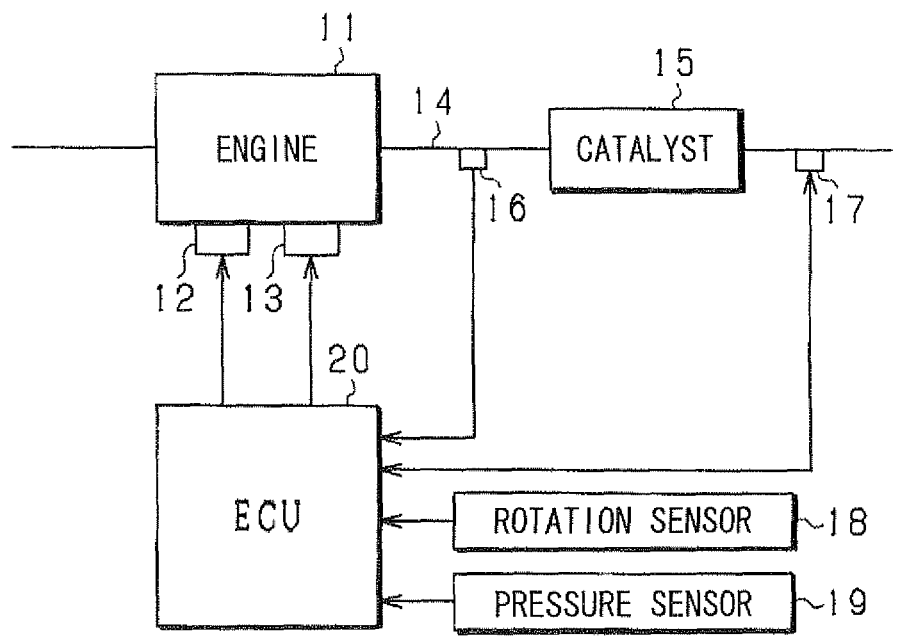
FIG. 1 is a schematic configuration diagram showing the outline of an engine control system according to an embodiment of the invention.

Hereinafter, an embodiment of the present invention will be described on the basis of the drawings. In this embodiment, a vehicle engine system with a vehicle-mounted engine is provided to monitor the amount of PM (conductive particulate matter) of exhaust gas exhausted from an engine. In particular, a PM sensor is provided in an engine exhaust pipe. Based on the amount of attached PM detected by the PM sensor, the amount of PM is monitored. FIG. 1 shows a configuration diagram of the outline of the system.

In FIG. 1, an engine 11 is a direct-injection gasoline engine. The engine 11 is provided with a fuel injection valve 12 and an igniter 13 which serve as an actuator for the operation of the engine 11. An exhaust pipe 14 of the engine 11 is provided with a three way catalyst 15 serving as an exhaust emission control system. An A/F sensor 16 is provided at an upstream side of the three way catalyst 15, and a PM sensor 17 as a particulate matter detection sensor is provided at a downstream side of the three way catalyst 15. The system is further provided with a rotation sensor 18 for detecting an engine rotational speed, a pressure sensor 19 for detecting the pressure of an intake pipe, and the like.

An ECU 20 mainly includes a microcomputer constructed of a well-known CPU, ROM, RAM, and the like. The ECU executes various control programs stored in the ROM to perform various control processes of the engine 11, based on the operating state of the engine. That is, the ECU 20 receives input of respective signals from the above sensors or the like, and controls the driving of the fuel injection valve 12 and the igniter 13 by computing the amount of injected fuel or the ignition timing based on the respective signals received.

The ECU 20 calculates the amount of PM actually exhausted from the engine 11 (actual PM emission amount) based on a detection signal from the PM sensor 17, and makes a diagnosis of the combustion state of the engine 11 based on the actual PM emission amount. Specifically, when the actual PM emission amount exceeds a predetermined value for determination of abnormality, it is determined that the amount of exhausted PM is excessive and that the engine becomes abnormal.

Further, the ECU 20 may variably control the control state of the engine 11 based on the actual PM emission amount calculated from the detection result of the PM sensor 17. For example, the ECU 20 can control the amount of injected fuel, the injection timing of fuel, and the ignition timing, based on the actual PM emission amount.

Figure 2:
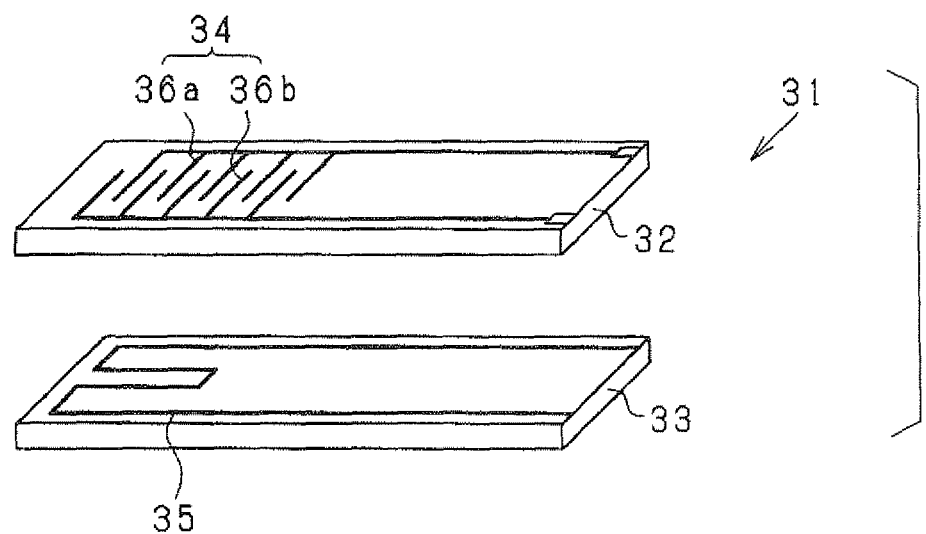
FIG. 2 is an exploded perspective view showing a main structure of a sensor element in a PM sensor.
Figure 3:
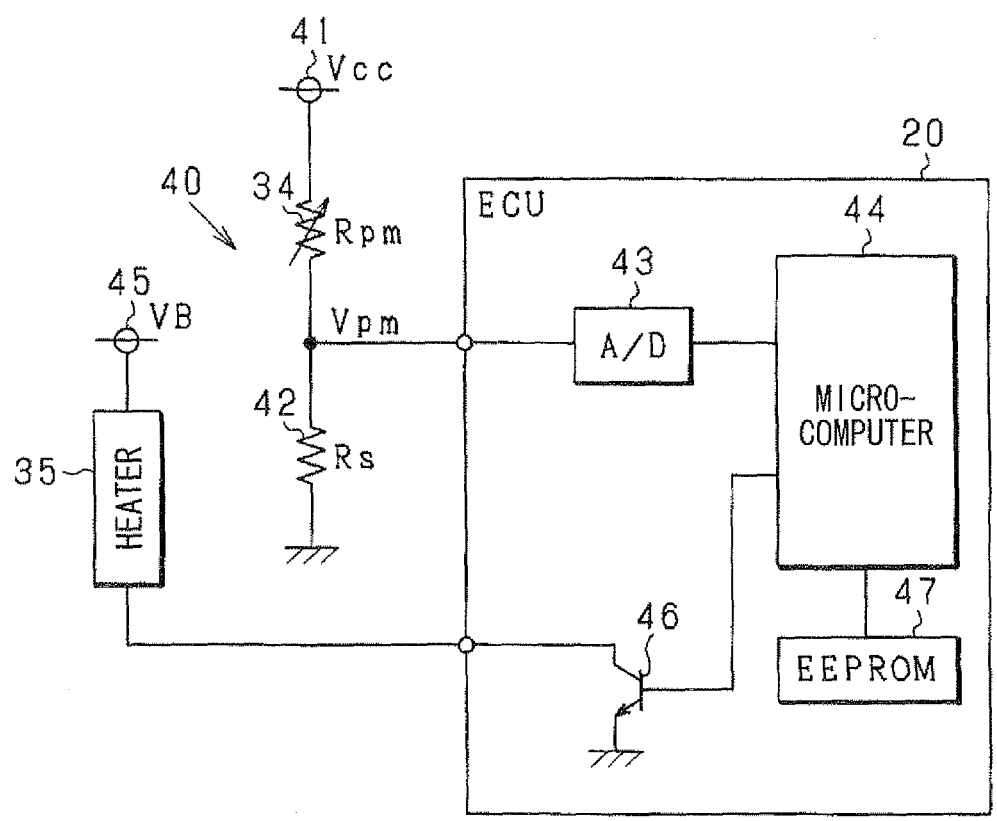
FIG. 3 is an electric configuration diagram regarding the PM sensor.

Next, the structure of the PM sensor 17, and the electric configuration of the PM sensor 17 will be described using FIGS. 2 and 3. FIG. 2 shows an exploded perspective view of the main structure of a sensor element 31 configured in the PM sensor 17, and FIG. 3 shows an electric configuration diagram regarding the PM sensor 17.

As shown in FIG. 2, the sensor element 31 includes two pieces of insulating substrates 32 and 33 having a longitudinal plate shape. One insulating substrate 32 is provided with a PM detector 34 for detecting the amount of PM. The other insulating substrate 33 is provided with a heater 35 for heating the sensor element 31. The sensor element 31 is a lamination structure in which two layers of the insulating substrates 32 and 33 are stacked with each other. The insulating substrate 32 corresponds to an attachment portion to which the particulate matter is attached and accumulated.

A pair of detection electrodes 36a and 36b are provided on the surface of the insulating substrate 32 opposite to the other insulating substrate 33, while being spaced apart from each other. The PM detector 34 is made of the pair of the detection electrodes 36a and 36b. Each of the detection electrodes 36a and 36b has a comb-like shape with teeth. The teeth of the combs of the detection electrodes 36a and 36b are alternatively arranged to be opposite to each other at predetermined intervals. The heater 35 includes a heating element made of, for example, an electrically-heated wire.

The shape of the pair of the detection electrodes 36a and 36b is not limited to the above-mentioned one, and may be a curved one. Alternatively, the detection electrodes 36a and 36b may be formed from a pair of electrode portions each of which is formed of one wire and which are arranged opposed to each other in parallel, while being spaced from each other by a predetermined distance.

Although not shown, the PM sensor 17 includes a holder for holding the sensor element 31. The sensor element 31 is fixed to an exhaust pipe with its one end held by the holder. In this case, a part including at least the PM detector 34 and the heater 35 is positioned in the exhaust pipe, while the PM sensor 17 is attached to the exhaust pipe with the insulating substrate 32 (PM attachment portion) of the sensor element 31 directed toward the upstream side of the exhaust gas. Thus, when exhaust gas containing PM flows through the exhaust pipe, the PM is attached and accumulated onto the detection electrodes 36a and 36b and its surroundings over the insulating substrate 32. The PM sensor 17 has a protective cover for covering protrusion parts of the sensor element 31.

When PM in the exhaust gas is attached and accumulated onto the insulating substrate 32 of the sensor element 31, the PM sensor 17 with the above structure detects the amount of PM using a change in resistance of the PM detector 34 (that is, resistance between the pair of detection electrodes 36a and 36b) which correspond to the amount of accumulated PM.

As shown in FIG. 3, the PM sensor 17 has the following electric configuration. That is, the PM detector 34 of the PM sensor 17 has one end thereof connected to a sensor power supply 41, and the other end thereof connected to a shunt resistor 42. The sensor power supply 41 is constructed of, for example, a constant-voltage circuit. The constant voltage Vcc is 5 V, for example. In this case, the PM detector 34 and the shunt resistor 42 form a voltage-dividing circuit 40, in which a voltage of an intermediate point is input as a PM detection voltage Vpm (sensor detection value) to the ECU 20. That is, in the PM detector 34, the resistance Rpm changes according to the amount of accumulated PM. The PM detection voltage Vpm is changed by the resistance Rpm and the resistance Rs of the shunt resistor 42. Then, the PM detection voltage Vpm is input to a microcomputer 44 via an A/D converter 43.

When Vcc=5 V and when Rs=5 kΩ, the PM detection voltage Vpm can be determined by the following formula (1):

$$Vpm = 5\ V \times 5\ k\Omega/(5\ k\Omega + Rpm) \tag{1}$$

At this time, when the amount of accumulated PM is 0 (or about 0), the resistance Rpm of the PM detector 34 becomes infinite, thereby resulting in Vpm=0 V. When the resistance Rpm of the PM detector 34 decreases, for example, decreases to 1 kΩ due to the accumulation of PM in the PM detector 34, the PM detection voltage Vpm becomes in Vpm=4.16V. In this way, the PM detection voltage Vpm changes according to the amount of accumulated PM at the PM detector 34. The microcomputer 44 calculates the amount of accumulated PM according to the PM detection voltage Vpm.

The voltage-dividing circuit 40 forms the signal output circuit. The PM detection voltage Vpm is variably changed by the voltage-dividing circuit 40 in an output range of 0 to 5 V. In this case, the output upper limit of the PM detection voltage Vpm is about 5 V, and strictly, slightly lower than 5 V, namely, 4.95V.

In this embodiment, particularly, when the PM is accumulated on the PM detector 34 as mentioned above, for example, when the resistance Rpm of the PM detector 34 becomes 1 kΩ, the PM detection voltage Vpm is "4.16 V", which is small as compared to the output upper limit (5V) of the PM detection voltage Vpm. This is because an increase in the PM detection voltage Vpm is taken into consideration during the forcible burning of the PM. The details thereof will be described later. The range of change in the PM detection voltage Vpm during the PM forcible burning is 4.16 to 5 V.

The heater 35 of the PM sensor 17 is connected to a heater power supply 45. The heater power supply 45 is, for example, a vehicle-mounted battery. The heater 35 is heated by power supplied from the vehicle-mounted battery. In this case, a transistor 46 is connected as a switching element to the lower side of the heater 35. The heating operation of the heater 35 is controlled by turning on/off the transistor 46 via the microcomputer 44.

When the energization of the heater 35 is started with the PM accumulated on the insulating substrate 32, the temperature of the accumulated PM increases, thereby forcedly burning the accumulated PM. Such forcible burning of the PM burns and removes the PM accumulated on the insulating substrate 32. For example, at the start of the engine, at the end of the operation of the engine, or when the amount of accumulated PM is determined to reach a predetermined amount, the microcomputer 44 determines that a request for forcible burning of the PM is made, and thus controls the heating operation of the heater 35.

Further, the ECU 20 is provided with an EEPROM 47 serving as a memory for a backup to store therein various types of studied values, abnormality diagnosis values (diagnostic data, or diagdata) or the like.

However, in the PM sensor 17, a sensor difference, a variation in an elapsed time, a circuit error or the like may be caused, and thereby the sensor output may be incorrectly detected. For example, if a foreign matter such as a metal piece or the like is attached to the insulating substrate 32 of the PM sensor 17, or if a weak leakage current flows with the impurities in the insulating substrate 32, a sensor output which originally should not be produced may be caused, or the sensor output may become larger than a predetermined value originally assumed.

Alternatively, the sensor output may be smaller than the predetermined value originally assumed.

In the present embodiment, the learning of the sensor output error is performed, and the sensor output is corrected by using the learned value, thereby removing the sensor output error. For example, when the sensor output error is larger than a predetermined value that is set beforehand, an output-error learning value (plus-side output error) is calculated based on a sensor output after the PM forcible burning. After the PM forcible burning, the accumulated PM on the insulating substrate 32 is burned and removed, and thereby the PM accumulated amount=0, and Vpm=0 V. However, if the sensor output error is caused, Vpm does not become zero (Vpm≠0 V). Thus, it is possible to calculate an output-error learning value based on the sensor output (i.e., PM detection voltage Vpm) after the PM forcible burning.

The output-error learning value obtained after the PM forcible burning corresponds to an output error after resetting the PM sensor 17 to an initial state, and is referred to as "zero-point learning value".

Furthermore, when the sensor output error is smaller than the predetermined value that is set beforehand, an output-error learning value (minus-side output error) is calculated based on a sensor output during the PM forcible burning. The PM adhering to and accumulated on the insulating substrate 32 has a temperature characteristic in which the resistance changes with respect to the temperature. For example, the resistance becomes smaller as the temperature becomes higher. During the PM forcible burning, because the resistance of the PM detector 34 is reduced, electrical current most easily flows between the detection electrodes 36a, 36b. In this case, the PM detection voltage Vpm is increased to the output upper-limit value, and is held at the output upper-limit value. However, if an output error is caused in the PM sensor 17, the PM detection voltage Vpm does not become the output upper-limit value (Vpm≠output upper-limit value). Thus, it is possible to calculate the output-error learning value during the PM forcible burning, based on the sensor output (i.e., PM detection voltage Vpm). In the present embodiment, the output upper-limit value is about 5 V, for example.

The output-error learning value obtained during the PM forcible burning corresponds to an output error of the output upper-limit value of the PM sensor 17, and is referred to as "upper-limit learning value".

Figure 4:
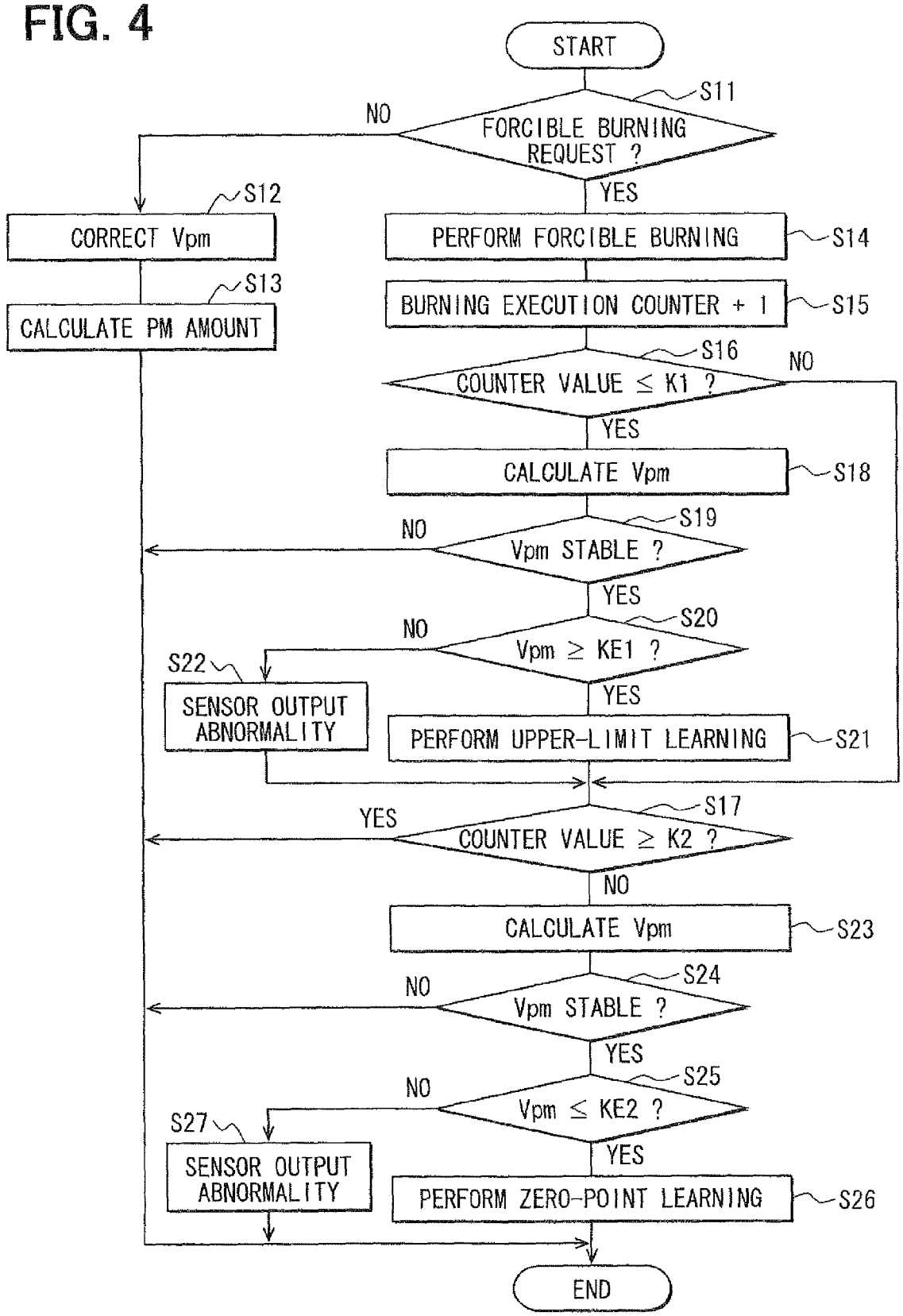
FIG. 4 is a flow diagram showing an output error learning process.

Next, the learning of the output error will be described in detail. FIG. 4 is a flow diagram showing a learning process of the sensor output error, which is repeatedly performed at a predetermined interval by the microcomputer 44.

Referring to FIG. 4, at step S11, it is determined whether or not a request for performing the forcible burning is made at the PM sensor 17. In this embodiment, a PM burning requirement flag is set by at lease one of the start time of operation of the engine 11, the end time of operation of the engine 11, a time where the amount of accumulated PM reaches a predetermined amount, and a time period of operation of the engine 11 or a time where vehicle traveling distance after the previous PM forcible burning process reaches a predetermined value, so that the forcible burning requirement is output.

When the request for the forcible burning is not determined, the operation proceeds to the step S12, without performing the PM forcible burning process and the learning process of the PM sensor 17. At step S12, the PM detection voltage Vpm is read as the detection signal of the PM sensor 17, and the PM detection voltage Vpm is corrected by using an output-error learning value. The output-error learning value is the zero-point learning value or the upper-limit learning value, calculated in the previous learning process, and can be suitably read from the EEPROM 47. Next, at step S13, a corrected PM detection voltage Vpm is calculated by using a map stored beforehand, and then the PM amount accumulated on the insulating substrate 32 is calculated.

When the forcible burning request is determined, the operation proceeds to step S14 so as to perform the PM forcible burning operation at the PM sensor 17. Specifically, the energization of the heater 35 for the PM sensor 17 is turned on so as to heat the PM sensor 17. Thereafter, at step S15, a burning execution counter is increased by 1.

A time delay is caused from when the heater 35 is turned on, to when the heater 35 becomes in a predetermined high-temperature state. That is, after a time passes from the heater 35 is turned on, the heater 35 becomes in the predetermined high-temperature state. Thus, the heater resistance is detected after the heater 35 is turned on, and the counting-up of the burning execution counter is started after the heater resistance reaches a predetermined value corresponding to the predetermined high-temperature state of the heater 35.

Thereafter, at step S16, S17, the count value of the burning execution counter is determined. That is, at step S16, it is determined whether or not the counter value of the burning execution counter is equal to or lower than a first determination value K1. When the counter value of the burning execution counter is larger than the first determination value K1 (i.e., the determination of Step S16 is NO), it is determined whether or not the counter value of the burning execution counter reaches a second determination value K2 that is larger than the first determination value K1. That is, K1<K2. The first determination value K1 is a threshold value for determining a time period from a start timing of the PM burning to a timing where the resistance value of the PM detector 34 begins to decrease. More specifically, the first determination value K1 is a threshold value for determining a time period required that the PM detection voltage Vpm reaches the output upper limit due to a decrease of the resistance of the PM detector 34, after the heater 35 is turned on. The second determination value K2 is a threshold value for determining whether a time period, required for finishing the burning and removing of the PM accumulated on the insulating substrate 32 due to the forcible burning, is elapsed.

When the counter value is equal to or lower than the first determination value K1 at step S16, an upper-limit learning process is performed in steps S18 to S22. In contrast, when the counter value is equal to or larger than the second determination value K2 at step S17, a zero-point learning process is performed in steps S23 to S27. When the counter value is larger than the first determination value K1 and is smaller than the second determination value K2, the control process is temporarily finished without performing the upper-limit learning process and the zero-point learning process.

When the upper-limit learning process is performed in a case where the counter value≤K1, the PM detection voltage Vpm is calculated at step S18, and it is determined whether the PM detection voltage Vpm is stable based on the calculated and obtained PM detection voltage Vpm. Step S19 determines whether the PM detection voltage Vpm is increased in accordance with heater energization. When a variation amount of the PM detection voltage Vpm is smaller than a predetermined value, it can determine that the PM detection voltage Vpm is stable at step S19. When the determination at step S19 is YES, it is determined whether the PM detection voltage Vpm is equal to or larger than an abnormality determination value KE1 at step S20. The abnormality determination value KE1 is a threshold value for determining whether an abnormality is caused in a case where the PM detection voltage Vpm is not increased to a predetermined voltage level in a previous burning period.

When the PM detection voltage Vpm is equal to or larger than KE1, an upper-time learning is performed at step S21. At this time, the present PM detection voltage Vpm is made as an upper-limit learning value, and the upper-limit learning value is stored in the EEPROM 47. The PM detection voltage Vpm, after the YES determinations at step S19 and S20, corresponds to a second sensor standard value. In a time period where the PM detection voltage Vpm is stable, the PM detection voltage Vpm or the mean value of the PM detection voltage Vpm may be calculated, and the calculated value (second sensor standard value) may be adapted as the upper-limit learning value. Alternatively, the values of Vpm with large variations may be not used in the calculation of the upper-limit learning value, or a corrected value of the previous learning value with a limited variation may be adapted as the upper-limit learning value.

When the determination of step S20 is NO, it is determined that the output of the PM sensor 17 has an abnormality. At this time, an abnormality diagnosis data for indicating an output abnormality of the PM sensor 17 is stored in the EEPROM 47.

On the other hand, when the zero-point learning process is performed in a case where the counter value K2, the PM detection voltage Vpm is calculated at step S23, and it is determined whether the PM detection voltage Vpm is stable based on the calculated and obtained PM detection voltage Vpm after the PM is burned and removed. Step S24 determines whether the PM detection voltage Vpm is decreased and converges to about 0 in accordance with the burning and removing of the PM. When a variation amount of the PM detection voltage Vpm is smaller than a predetermined value, it can determine that the PM detection voltage Vpm is stable at step S24. When the determination at step S24 is YES, it is determined whether the PM detection voltage Vpm is equal to or smaller than an abnormality determination value KE2 at step S25. The abnormality determination value KE2 is a threshold value for determining whether an abnormality is caused in a case where the PM detection voltage Vpm is not decreased to a predetermined voltage level after the PM is burned and removed.

When the PM detection voltage Vpm is equal to or smaller than KE2, the zero-point learning is performed at step S26. At this time, the present PM detection voltage Vpm is made as a zero-point learning value, and the zero-point learning value is stored in the EEPROM 47. The PM detection voltage Vpm after the YES determinations at step S24 and S25 corresponds to a first sensor standard value. In a time period where the PM detection voltage Vpm is stable, the PM detection voltage Vpm or the mean value of the PM detection voltage Vpm may be calculated, and the calculated value (first sensor standard value) may be adapted as the zero-point learning value. Alternatively, the values of Vpm with large variations may be removed in the calculation of the upper-limit learning value, or a corrected value of the previous learning value with a limited variation may be adapted as the upper-limit learning value.

When the determination of step S25 is NO, it is determined whether the output of the PM sensor 17 has an abnormality. At this time, an abnormality diagnosis data for indicating an output abnormality of the PM sensor 17 is stored in the EEPROM 47.

FIG. 5 is a timechart for explaining the output error learning process.

Referring to FIG. 5, at the timing t1, a PM burning requirement flag is set to start the energization of the heater 35 at the PM sensor 17, so as to increase a heater resistance. Specifically, at the timing t1, the value of the burning execution counter is updated. After the timing t1, the temperature of the accumulated PM on the PM sensor 17 (insulating substrate 32) increases so as to decrease the resistance between the electrodes 36a, 36b, thereby increasing the PM detection voltage Vpm.

In the period from the timing t1 to the timing t2, the resistance (PM resistance) of the pair of electrodes 36a, 36b decreases in accordance with a heating start of the heater 35, and thereby the PM detection voltage Vpm is increased to the output upper-limit value and is held at the output upper-limit value. Thus, in the period from the timing t1 to the timing t2, the upper-limit learning can be performed. The solid line of the time chard regarding the Vpm indicates the normal values, in FIG. 5. When the present PM detection voltage Vpm is smaller than the normal value as in the chain line of FIG. 5, the present PM detection voltage Vpm is calculated as the upper-limit learning value. At the timing t2, the burning execution counter becomes equal to or larger than K1, and the upper-limit learning is ended and the upper-limit learning end flag is set.

After the timing t2, the accumulated PM is burned and removed, so that the resistance (PM resistance) between the pair of the detection electrodes 36a, 36b is increased, and the PM detection voltage Vpm is rapidly decreased to about 0 V. At the timing t3, the burning execution counter reaches K2, and it is determined that the burning and removing of the PM is ended. At this time, the PM burning end flag is set, and the zero-point learning is started. The solid line of the time chard regarding the Vpm indicates the normal value, in FIG. 5. When the present PM detection voltage Vpm is larger than the normal value as in the chain line of FIG. 5 after the timing t2, the present PM detection voltage Vpm is calculated as the zero-point learning value. At the timing t3, the zero-point learning is ended, and the zero-point learning end flag is set.

In FIG. 5, the upper-limit shift of the PM detection voltage Vpm and the zero-point shift thereof are indicated by the same time chart. However, actually, the upper-limit shift of the PM detection voltage Vpm and the zero-point shift thereof are not caused at the same time, and may be respectively caused. Furthermore, FIG. 5 shows a normal operation in which the PM detection voltage Vpm during the PM burning is equal to or larger than KE1, and the PM detection voltage Vpm after the burning and removing the PM is equal to or smaller than KE2.

At the timing t4, the heater 35 is turned off because of the end of a series of forcible burning processes, and the PM burning requirement flag is reset.

Figure 6A:
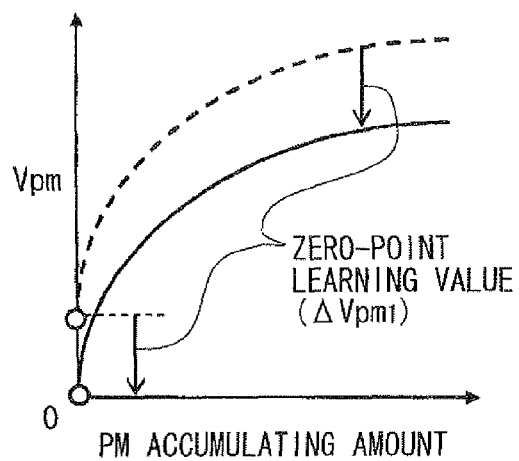
FIGS. 6A and 6B are graphs showing sensor output corrections by using a zero-point learning value.
Figure 6B:
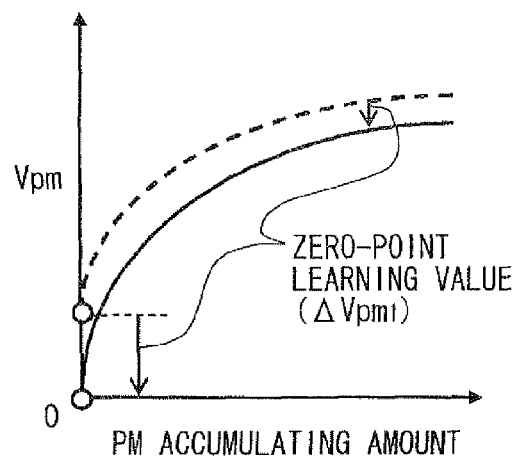
Figure 7A:
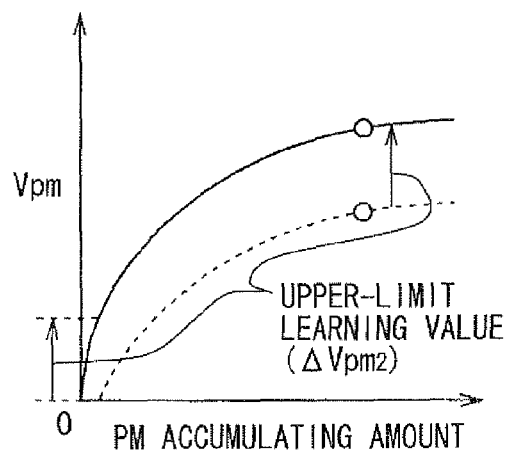
FIGS. 7A and 7B are graphs showing sensor output corrections by using an upper-limit learning value.
Figure 7B:
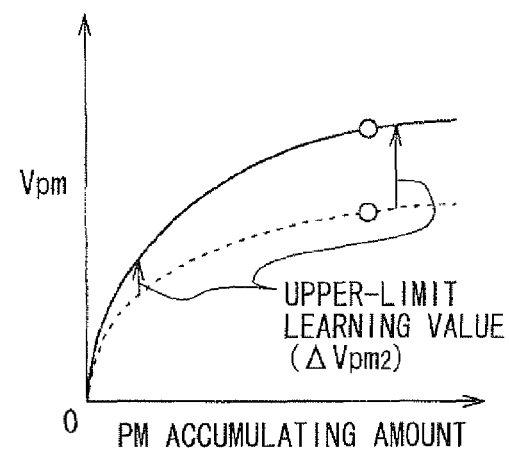

FIGS. 6A, 6B, 7A and 7B are graphs showing sensor output corrections by using output error learning values. FIGS. 6A and 6B show zero-point learning values in which the zero-point of the PM detection voltage is shifted to the positive side with respect to the normal value, and FIGS. 7A and 7B show upper-limit learning values in which the upper-limit of the PM detection voltage is shifted to the negative side with respect to the normal value. In the graphs of FIGS. 6A, 6B, 7A and 7B, the solid lines indicate the normal sensor output characteristics in which the output error is not caused, and the chain lines indicate the sensor output characteristics in which the sensor output error is caused.

The PM detection voltage Vpm is adapted as an example of the output characteristics of the PM sensor 17. The PM detection voltage Vpm changes in accordance with the PM accumulating amount on the PM detector 34. In a case where the output error is not caused, the PM detection voltage Vpm becomes zero when the PM accumulating amount is zero, and the PM detection voltage Vpm gradually increase as the PM accumulating amount increases. Because the PM detection voltage Vpm is detected by using the voltage-dividing circuit 40, the output characteristics of the PM detection voltage Vpm becomes in non-linear. For example, the PM detection voltage Vpm is gradually approached to the voltage Vcc (5V) in accordance with an increase of the PM accumulating amount, and becomes stable immediately before reaching the Vcc (5V).

Furthermore, the sensor output error may be caused such that the sensor output value (chain line graph) is larger than a predetermined normal value (solid line graph) as shown in FIGS. 6A and 6B. In this case, the PM detection voltage Vpm is corrected to be smaller with respect to the sensor output characteristic graph. As shown in the graph of FIG. 6A, the zero-point learning value is obtained in the zero-point learning process as a correction value ΔVpm1 of the Vpm, and the sensor output characteristic is corrected by the correction amount so that the detected Vpm is reduced by the same ratio with respect to the increase of the PM accumulating amount, in the entire area of the PM accumulating amount. That is, a different between the detected Vpm (chain-line graph in FIG. 6A) and the normal value (solid-line graph in FIG. 6A) is set as the correction value ΔVpm1 that is increased by the same ratio as the increase of the PM accumulating amount.

Alternatively, as shown in FIG. 6B, the correction value ΔVpm1 of the Vpm may be calculated based on the zero-point learning value in a case where the PM accumulating amount is zero and in a case where the PM accumulating amount is larger than zero, and then the correction of the sensor output characteristic may be performed in accordance with the respective correction values ΔVpm1 of the Vpm. For example, as shown in FIG. 6B, the zero-point learning value may be set as the correction amount ΔVpm1 of the Vpm when the PM accumulating amount is zero. In this case, the correction amount ΔVpm1 of the Vpm may be set based on respective PM accumulating amounts, such that the correction amount ΔVpm1 of the Vpm becomes smaller as the PM accumulating amount is larger. That is, a different between the detected Vpm (chain-line graph in FIG. 6B) and the normal value (solid-line graph in FIG. 6B) is set as the correction value ΔVpm1 that becomes smaller as the PM accumulating amount becomes larger. Thus, the sensor output characteristic is corrected so that the Vpm is reduced by the correction amount ΔVpm1, and the correction amount ΔVpm1 is changed based on the PM accumulating amount.

Furthermore, the sensor output error may be caused such that the sensor output value (chain line graph) is smaller than a predetermined normal value (solid line graph) as shown in FIGS. 7A and 7B. In this case, the PM detection voltage Vpm is corrected larger with respect to the sensor output characteristic. As shown in the graph of FIG. 7A, the upper-point learning value is obtained in the upper-point learning process as a correction value ΔVpm2 of the Vpm, and the sensor output characteristic is corrected by the correction amount ΔVpm2 so that the detected Vpm is increased by the same ratio with respect to an increase of the PM accumulating amount, in the entire area of the PM accumulating amount. That is, a different between the detected Vpm (chain-line graph in FIG. 7A) and the normal value (solid-line graph in FIG. 7A) is set as the correction value ΔVpm2 that is increased by the same ratio as the increase of the PM accumulating amount.

Alternatively, as shown in FIG. 7B, the correction value ΔVpm2 of the Vpm may be calculated based on the PM accumulating amount, and then the correction of the sensor output characteristic graph may be performed in accordance with the correction value ΔVpm2 of the Vpm. For example, in a stable area of the Vpm, the upper-limit learning value may be used as the correction value ΔVpm2 of the Vpm, so that the correction amount ΔVpm2 of the Vpm is made smaller as the PM accumulating amount becomes smaller, and the correction amount ΔVpm2 of the Vpm becomes zero when the PM accumulating amount is zero, as shown in FIG. 7B. Thus, the sensor output characteristic is corrected to be larger by the correction amount ΔVpm2. As shown in FIG. 7B, the correction amount is increased as the PM accumulating amount increases.

According to the present embodiment, the PM detection voltage Vpm is calculated in a state where the PM is burned and removed from the insulating substrate 32 as a first sensor standard value, based on the PM detection voltage Vpm obtained immediately after the burning and removing of the PM, and is stored as the zero-point learning value. Thus, it is possible to determine an error even in a case where the PM detection voltage Vpm after the burning and removing of the PM is not an ordinary value when the PM accumulating amount is zero. Therefore, correction can be accurately performed with respect to the PM detection voltage Vpm. As a result, a detection error of the PM sensor 17 can be removed, and the PM accumulating amount can be accurately detected by using the PM sensor 17.

According to the present embodiment, the PM detection voltage Vpm is calculated in a state where the resistance of the PM detector 34 is reduced based on the PM detection voltage Vpm during the burning of the PM, as a second sensor standard value, and is stored as the upper-limit learning value. Thus, it is possible to determine a detection error even in a case where the PM detection voltage Vpm during the PM burning is not ordinary value (output upper limit). Therefore, the PM detection voltage Vpm can be suitably corrected.

According to the present embodiment, the upper-limit learning and the zero-point learning are performed. Therefore, the detection error of the PM sensor 17 can be effectively corrected in a case where the PM accumulating amount is zero and in a case where the sensor output is around the upper limit side.

In the present embodiment, the voltage-dividing circuit 40 is configured by the PM detector 34 and the shunt resistor 42, such that the PM detection voltage Vpm is output as a voltage at a middle point between the PM detector 34 and the shunt resistor 42. Therefore, a detection error of the PM sensor 17, including a circuit error, can be effectively removed.

In the present embodiment, the PM detection voltage Vpm is corrected by using different correction amounts based on the zero-point learning value, in a case where the PM accumulating amount is zero and in a case where the PM accumulating amount is larger than zero. Thus, even when the PM detection voltage Vpm is corrected by using the zero-point learning value, the correction of the PM detection voltage Vpm can be suitably performed in a wide range of the PM accumulating amount.

Furthermore, the PM detection voltage Vpm can be corrected by using different correction values in accordance with the PM accumulating amount based on the upper-limit learning value. Thus, even when the PM detection voltage Vpm is corrected based on the upper-limit learning value, the correction of the PM detection voltage Vpm can be suitably performed in a wide range of the PM accumulating amount.

In the present embodiment, the diagnosis of abnormality is performed based on the PM detection voltage Vpm obtained during the PM burning by using the heating of the heater 35 or based on the PM detection voltage Vpm obtained immediately after the burning and removing of the PM is finished.

Then, after the heating of the heater 35 is started, the PM detection voltage Vpm is changed so that the resistance value of the PM detector 34 is increased. Furthermore, the PM detection voltage Vpm obtained within a predetermined change range is used as the zero-point learning value. Therefore, the zero-point learning value can be accurately calculated even in a case where the detection error of the PM sensor 17 is caused and the PM detection voltage Vpm does not become zero.

After the heating of the heater 35 is started, the PM detection voltage Vpm is changed so that the resistance value of the PM detector 34 is decreased. Furthermore, the PM detection voltage Vpm obtained within a predetermined change range is used as the upper-limit learning value. Therefore, the upper-limit learning value can be accurately calculated even in a case where the detection error of the PM sensor 17 is caused and the PM detection voltage Vpm does not become the upper-limit learning value.

Other Embodiments

The present invention is not limited to the contents disclosed in the above embodiment, and may be applied as follows.

The upper limit learning value may be suitably calculated as follows. For example, in the PM forcible burning period, a maximum value Vmax of the PM detection voltage Vpm may be calculated by a peak hold processing, and the upper limit learning value can be calculated based on the maximum value Vmax of the PM detection voltage Vpm. In this case, it can prevent the upper limit learning from being performed based on the sensor output before the PM detection voltage Vpm reaches the output upper-limit value or based on the sensor output after the PM detection voltage Vpm is reduced so as to increase the resistance value of the PM detector 34. Thus, the correction of the sensor detection value can be suitably performed.

In the above embodiment, the voltage-dividing circuit 40 shown in FIG. 3 is used as the signal output circuit. However, connection between the PM detector 34 and the shunt resistor 42, for forming the voltage-dividing circuit may be set reversely. Specifically, the PM detector 34 may be provided on the lower side, and the shunt resistor 42 may be provided on the higher side. In this arrangement, the PM detection voltage Vpm is determined by the following formula (2):

$$Vpm = 5\,V \times Rpm/(Rs+Rpm) \qquad (2)$$

in which Rpm is a resistance of the PM detector 34, and Rs is a resistance (for example, 5 kΩ) of the shunt resistor 42.

In such a case, when the amount of accumulated PM is 0 (or about 0), the Vpm is 5 V (Vpm=5V). The value of 5 V corresponds to the origin (0 point). When the resistance Rpm of the PM detector 34 decreases to, for example, 1 kΩ due to the accumulation of PM, the Vpm is 0.83 V (Vpm=0.83V). The range of a voltage of the voltage-dividing circuit 40 is 0 to 5 V. The range of change in the PM detection voltage Vpm during the PM forcible burning is 0 to 0.83 V.

In the above described embodiment, a state immediately after the burning and removing of the PM may be determined and the zero-point learning may be performed, when any one of the condition, where the burning execution counter is equal to or larger than K2, and the condition, where the PM detection voltage Vpm is stable after burning and removing the PM, is satisfied.

Furthermore, the upper-limit learning may be performed, when any one of the condition, where the burning execution counter is equal to or smaller than K1, and the condition, where the PM detection voltage Vpm is stable after the PM detection voltage Vpm is increased due to the start of the heater 35, is satisfied.

Furthermore, a heater resistance calculating means for calculating a heater resistance may be provided. In this case, a state during the PM burning or a state immediately after the burning and removing the PM may be determined based on the calculated heater resistance, and the zero-point learning or the upper-limit learning may be performed. The heater resistance calculating means detects a heater resistance voltage and a heater current when the heater 35 is turned on, and the heater resistance value can be calculated based on the detected value. In this case, when the heater resistance is changed to be decreased after the heating of the PM due to the heater 35 is started, it is determined that the PM sensor 17 is in a state immediately after burning and removing the PM. In this case, the PM detection voltage Vpm is obtained and the zero-point learning is performed. When the detection value of the heater resistance is increased after the heating of the PM starts, it is determined that the PM sensor 17 is in the PM burning. In this case, the PM detection voltage Vpm may be obtained and the upper-limit learning may be performed.

Alternatively, an electrical power amount consumed in the heater 35 after being turned on may be calculated. In this case, a state immediately after burning and removing the PM may be determined based on the consumed electrical power amount, and the zero-point learning may be performed. Furthermore, a PM burning state may be determined based on the consumed electrical power, and the upper-limit learning may be performed in the PM burning state.

Alternatively, a sensor or the like for detecting a sensor element temperature or an exhaust gas temperature may be provided at a downstream side of the PM sensor 17 in the exhaust passage. In this case, a PM burning state may be determined based on the detected temperature of the sensor, and the upper-limit learning may be performed in the PM burning state. Furthermore, a state immediately after the burning and removing of the PM may be determined based on the detected temperature, and the zero-point learning may be performed. For example, when the detected temperature is increased or is higher than a predetermined temperature, it is determined that the PM sensor 17 is in the PM burning state. In contrast, when the detected temperature is decreased, it is determined that the PM sensor 17 is in a state immediately after the burning and removing of the PM.

In the present embodiment, the diagnosis of abnormality of the PM sensor 17 is performed based on a variation amount of the PM detection voltage Vpm obtained in the PM burning state or in a state immediately after the burning and removing the PM. At this time, when the variation amount of the PM detection voltage Vpm is equal to or larger than a determination value, an abnormality can be determined.

In the above-described embodiment, the zero-point learning may be performed regardless of whether the PM detection voltage Vpm is equal to or smaller than the abnormality determination value KE2. In this case, an abnormality diagnosis of the PM sensor 17 may be performed based on the zero-point learning value obtained by the zero-point learning process. When the zero-point learning value is outside of a predetermined variation range, it is determined that the PM sensor 17 has an abnormality.

In the above-described embodiment, the upper-limit learning may be performed regardless of whether the PM detection voltage Vpm is equal to or larger than the abnormality determination value KE1. In this case, an abnormality diagnosis of the PM sensor 17 may be performed based on the upper-limit learning value obtained by the upper-limit learning process. When the upper-limit learning value is outside of a predetermined variation range, it is determined that the PM sensor 17 has an abnormality.

In the above embodiment, the heater 35 is provided in the insulating substrate 32 of the PM sensor 17 as heating means for the PM forcible burning. However, the heating means may be configured by using gas in an exhaust pipe, so that the temperature around the PM sensor 17 is increased to a temperature at which the PM can be burned (for example, of 650° C.). In this case, the exhaust temperature can be increased by burning control of the engine, or an additional heater may be provided in the exhaust pipe.

The PM sensor 17 may be disposed on at least one of the downstream and upstream sides of a PM filter provided in an engine exhaust pipe and adapted for collecting PM. Further, based on a detected value of the PM sensor, the timing of reproducing the PM filter may be controlled. Alternatively, or additionally, based on the detected value of the PM sensor, the diagnosis of abnormality of the PM filter may be carried out.

The sensor controller of above embodiment is applied to the direct-injection gasoline engine, but can be applied to other types of engines. For example, the sensor controller may be applied to a diesel engine (especially, a direct injection engine), and may be adapted to the PM sensor provided in an exhaust pipe of the diesel engine. The amount of PM contained in other kinds of gas except for the exhaust gas from the engine may be detected.

Although the present invention has been fully described in connection with the preferred embodiments thereof with reference to the accompanying drawings, it is to be noted that various changes and modifications will become apparent to those skilled in the art.

For example, according to an aspect of the above-described embodiment and modifications, a sensor controller is adapted to a particulate matter detection sensor 17. The particulate matter detection sensor 17 includes an attachment portion (e.g., insulating substrate 32) to which conductive particulate matter contained in gas is attached, and a pair of opposed electrodes (e.g., detection electrodes 36a, 36b) spaced from each other at the attachment portion. Furthermore, the particulate matter detection sensor 17 is adapted to output a detection signal corresponding to a resistance between the pair of opposed electrodes. The sensor controller is adapted to calculate an amount of attached particulate matter based on a sensor detection value from the particulate matter detection sensor 17. In this case, the sensor controller includes: a heater 35 configured to heat the attachment portion so as to burn and remove the particulate matter attached to the attachment portion; learning means for obtaining the sensor detection value immediately after burning and removing the particulate matter due to heating of the heater 35, for calculating a first sensor standard value based on the obtained sensor detection value in a state where the particulate matter is removed from the attachment portion, and for storing the first sensor standard value as a first learning value; and correcting means for correcting the sensor detection value based on the first sensor standard value stored by the learning means. Here, the heater 35 may include a heating unit for burning and removing the particulate mater by using the heat generated from the heater unit, and a heating means for heating the exhaust gas to a burning temperature of the particulate matter so as to burn the particulate matter, and the like.

Thus, even in a case where the first sensor standard value does not become a predetermined value that is set when the amount of attached particulate matter is zero, an error of the particulate matter detection sensor can be determined, and the sensor detection value can be accurately corrected. As a result, a detection error of a particulate matter detection sensor (PM sensor) can be effectively reduced, and thereby the amount of attached particulate matter can be accurately detected.

The sensor controller may further include a voltage-dividing circuit 40 that has an electrode resistance corresponding to the resistance of the pair of opposed electrodes, a shunt resistance and an electrical source portion. In this case, the voltage-dividing circuit 40 is configured to output a voltage at a middle point between the electrode resistance and the shunt resistance as the sensor detection value, and the learning means obtains the voltage at the middle point immediately after the burning and removing of the particulate matter and calculates the first sensor standard value based on the voltage at the middle point. Therefore, detection error of the particulate matter detection sensor including a circuit error can be effectively removed.

The correcting means may calculate correction values that are different from each other in accordance with the amounts of the attached particulate matter including a case without the attached particulate matter based on the first sensor standard value, and corrects the sensor detection value by using the calculated correction values. In this case, the correcting means may calculate the correction value based on the first sensor standard value, such that the correction value is smaller as the amount of the attached particulate matter becomes larger, and is smaller than a correction value in a case where the amount of the attached particulate matter is zero.

Furthermore, the learning means may obtain the sensor detection value in a state where the resistance between the pair of opposed electrodes varies to be increased and a variation amount of the resistance is within a predetermined range, and calculates the first sensor standard value based on the obtained sensor detection value.

The sensor controller may further include abnormality diagnosis means for performing diagnosis of abnormality of the particulate matter detection sensor based on the sensor detection value obtained immediately after burning and removing of the particulate matter.

The particulate matter detection sensor may be connected to a signal output circuit such that the sensor detection value is changeable in a predetermined output range by the signal output circuit. Furthermore, the learning means may obtain the sensor detection value in a burning of the particulate matter due to heating of the heater, calculates a second sensor standard value in a state where the resistance between the pair of opposed electrodes is reduced based on the obtained sensor detection value, and stores the second sensor standard value as a second learning value. In this case, the correcting means may correct the sensor detection value based on at least one of the first sensor standard value and the second sensor standard value stored by the learning means.

The signal output circuit may be a voltage-dividing circuit 40 that has an electrode resistance corresponding to the resistance of the pair of opposed electrodes, a shunt resistance and an electrical source portion. In this case, the voltage-dividing circuit 40 may be configured to output a voltage at a middle point between the electrode resistance and the shunt resistance as the sensor detection value, and the learning means obtains the voltage at the middle point in the burning of the particulate matter, and calculates the second sensor standard value based on the voltage at the middle point. Even in this case, the correcting means may calculate correction values that are different from each other in accordance with the amounts of the attached particulate matter based on the second sensor standard value, and may correct the sensor detection value by using the calculated correction values.

The learning means may obtain the sensor detection value in a state where the resistance between the pair of opposed electrodes varies to be decreased and a variation amount of the resistance is within a predetermined range, and may calculate the second sensor standard value based on the obtained sensor detection value.

Furthermore, the correcting means may calculate the correction value based on the second sensor standard value, such that the correction value is smaller as the amount of the attached particulate matter becomes smaller and is larger as the amount of the attached particulate matter becomes larger.

Such changes and modifications are to be understood as being within the scope of the present invention as defined by the appended claims.

What is claimed is:

1. A sensor controller system configured to control the operation of an engine,
    the sensor controller system comprising:
    a particulate matter detection sensor; and
    a sensor controller comprising:
    a heater connected to the particulate matter detection sensor, the particulate matter detection sensor including an attachment portion to which conductive particulate matter contained in gas is attached, and a pair of opposed electrodes spaced from each other at the attachment portion, the heater heating, via the pair of opposed electrodes, the attachment portion so as to burn and remove the particulate matter attached to the attachment portion; and
    a computer processor connected to the particular matter detection sensor and the engine, the computer processor performing at least
    obtaining a sensor detection value, corresponding to a resistance between the pair of opposed electrodes, outputted from the particulate matter detection sensor immediately after the burning and removing the particulate matter due to heating of the heater,
    calculating a first sensor standard value based on the obtained sensor detection value in a state where the particulate matter is removed from the attachment portion,
    storing the first sensor standard value as a first learning value
    correcting a sensor detection value outputted from the particulate matter detection sensor based on the stored first sensor standard value,
    calculating an amount of attached particulate matter based on the corrected sensor detection value,
    outputting a control signal to the engine based on the calculated amount of attached particulate matter, and
    controlling the operation of the engine.

2. The sensor controller system according to claim 1, wherein
    the computer processor is configured to further perform calculating correction values that are different from each other in accordance with the amounts of the attached particulate matter, based on the first sensor standard value, and correcting the sensor detection value by using the calculated correction values.

3. The sensor controller system according to claim 1, wherein the computer processor is configured to further perform
    diagnosis of abnormality of the particulate matter detection sensor based on the sensor detection value obtained immediately after burning and removing of the particulate matter.

4. The sensor controller system according to claim 1, wherein
    the computer processor is configured to further perform obtaining the sensor detection value in a state where the resistance between the pair of opposed electrodes varies to be increased and a variation amount of the resistance is within a predetermined range, and calculating the first sensor standard value based on the obtained sensor detection value.

5. The sensor controller system according to claim 1, wherein
    the particulate matter detection sensor is connected to a signal output circuit such that the sensor detection value is changeable in a predetermined output range by the signal output circuit,
    the learning means obtains the sensor detection value in a burning of the particulate matter due to heating of the heater, calculates a second sensor standard value in a state where the resistance between the pair of opposed electrodes is reduced based on the obtained sensor detection value, and stores the second sensor standard value as a second learning value; and
    the correcting means corrects the sensor detection value based on at least one of the first sensor standard value and the second sensor standard value stored by the learning means.

6. The sensor controller system according to claim 5, wherein
    the signal output circuit is a voltage-dividing circuit that has an electrode resistance corresponding to the resistance of the pair of opposed electrodes, a shunt resistance and an electrical source portion,
    the voltage-dividing circuit is configured to output a voltage at a middle point between the electrode resistance and the shunt resistance as the sensor detection value, and
    the learning means obtains the voltage at the middle point in the burning of the particulate matter, and calculates the second sensor standard value based on the voltage at the middle point.

7. The sensor controller system according to claim 6, wherein
    the correcting means calculates correction values that are different from each other in accordance with the amounts of the attached particulate matter based on the second sensor standard value, and corrects the sensor detection value by using the calculated correction values.

8. The sensor controller system according to claim 5, further comprising abnormality diagnosis means for performing diagnosis of abnormality of the particulate matter detection sensor based on the sensor detection value in the burning of the particulate matter.

9. The sensor controller system according to claim 5, wherein the learning means obtains the sensor detection value in a state where the resistance between the pair of opposed electrodes varies to be decreased and a variation amount of the resistance is within a predetermined range, and calculates the second sensor standard value based on the obtained sensor detection value.

10. The sensor controller system according to claim 2, wherein the computer processor is configured to further perform calculating the correction value based on the first sensor standard value, such that the correction value is smaller as the amount of the attached particulate matter becomes larger.

11. The sensor controller system according to claim 7, wherein the correcting means calculates the correction value based on the second sensor standard value such that the correction value is smaller as the amount of the attached particulate matter becomes smaller and is larger as the amount of the attached particulate matter becomes larger.

12. The sensor controller system according to claim 4, wherein the particulate matter detection sensor further comprises a voltage-dividing circuit that comprises the pair of opposed electrodes of the attachment portion, a shunt resistance and an electrical source portion, and has an electrode resistance corresponding to the resistance of the pair of opposed electrodes, wherein the voltage-dividing circuit is configured to output a voltage at a middle point between the electrode resistance and the shunt resistance as the sensor detection value, and wherein the computer processor is further configured to perform obtaining the voltage at the middle point immediately after the burning and removing of the particulate matter, and calculating the first sensor standard value based on the voltage at the middle point.

* * * * *